United States Patent [19]

Tejeiro

[11] Patent Number: 5,172,845
[45] Date of Patent: Dec. 22, 1992

[54] RIGHT ANGLE ARTICULATED INTESTINAL STAPLER

[76] Inventor: William V. Tejeiro, 3980 Kumquat Ave., Coconut Grove, Fla. 33133

[21] Appl. No.: 684,224

[22] Filed: Apr. 12, 1991

[51] Int. Cl.⁵ .......................................... A61B 17/072
[52] U.S. Cl. ...................................... 227/180; 227/19; 227/178
[58] Field of Search .......................... 227/180, 19, 178

[56] References Cited

U.S. PATENT DOCUMENTS

| | | | |
|---|---|---|---|
| 2,016,466 | 10/1935 | Vogel | 227/134 X |
| 4,290,542 | 9/1981 | Fedotov et al. | 227/155 |
| 4,566,620 | 1/1986 | Green et al. | 227/19 |
| 4,617,928 | 10/1986 | Alfranca | 227/19 X |
| 4,684,051 | 8/1987 | Akopov et al. | 227/19 |

Primary Examiner—Douglas D. Watts
Assistant Examiner—Rinaldi Rada
Attorney, Agent, or Firm—Larson & Taylor

[57] ABSTRACT

The intestinal stapler includes a L-shaped base and a detachable L-shaped staple actuator arm. An attachment mechanism, for pivotally, detachably mounting the staple actuator arm to the base is provided such that the staple actuator arm pivots with respect to the base from an open position for receiving a bowel section, and a closed position, for securing the bowel section. A staple firing mechanism is provided for stapling the secured bowel section, and a blade is provided for severing the bowel section after stapling. The L-shaped base and actuator arm are detachable thus providing for precise positioning of the stapler within the abdominal cavity of a patient for safe and efficient bowel resections.

5 Claims, 6 Drawing Sheets

RIGHT ANGLE ARTICULATED INTESTINAL STAPLER

FIELD OF THE INVENTION

The invention generally relates to surgical devices and in particular to an intestinal stapling device for use in resections and anastomosis of bowels or other tissue.

BACKGROUND OF THE INVENTION

Various intestinal staplers have been devised for stapling bowel sections. A typical intestinal stapler includes a relatively long handle with a trigger mechanism at one end thereof and a jaw disposed at the other end of the handle. The jaw includes both a staple actuator and anvil assembly. In use, a bowel section must be securely and precisely positioned within the stapling jaw. However, prior art devices have not provided adequate means for securing the bowel section within the stapling jaw, and thus in use, the bowel section frequently slips within, or completely out of, the stapling jaw.

Patent examples of such devices are described in U.S. Pat. Nos. 3,494,533 (Green et al), 4,429,695 (Green), 4,354,628 (Green), 4,520,817 (Green), 4,522,327 (Korthoff et al), 4,530,453 (Green), 4,665,916 (Green), 4,741,336 (Failla et al), and 4,788,978 (Strekopytov et al).

SUMMARY OF THE INVENTION

In accordance with the invention, an intestinal stapler is provided comprising a generally L-shaped base including an elongated handle with an anvil on one end thereof, a generally L-shaped staple actuator arm having a trigger mechanism at one end thereof and stapler means at the other end thereof, attachment means for pivotally, detachably mounting the actuator arm on the base such that the actuator arm is pivotally mounted with respect to the base and is movable between an open and a closed position. In the open position a gap is formed between the stapler means and the anvil, for receiving tissue to be stapled. In the closed position the stapler abuts against the anvil to substantially close the gap and secure the tissue.

Preferably, the attachment means comprises a plurality of hook members, fixed to one end of the anvil on the base and hook receiving members disposed on one end of the stapler means for detachably, pivotally receiving the hook members. A blade means may be provided on the stapler means for severing tissue disposed between the actuator arm and the anvil.

The intestinal stapler of the invention with its detachable staple actuator arm and anvil assembly, provides a means for precisely and securely positioning a bowel section or other tissue for quick and precise stapling or severing. Further, the L-shaped configuration of the separable actuator arm and anvil assembly allows access to bowel sections not easily accessible by prior art devices.

Other features and advantages of the invention will be apparent from the detailed description of the invention which follows.

DETAILED DESCRIPTION OF THE PREFERRED EMBODIMENT

Figure 1:
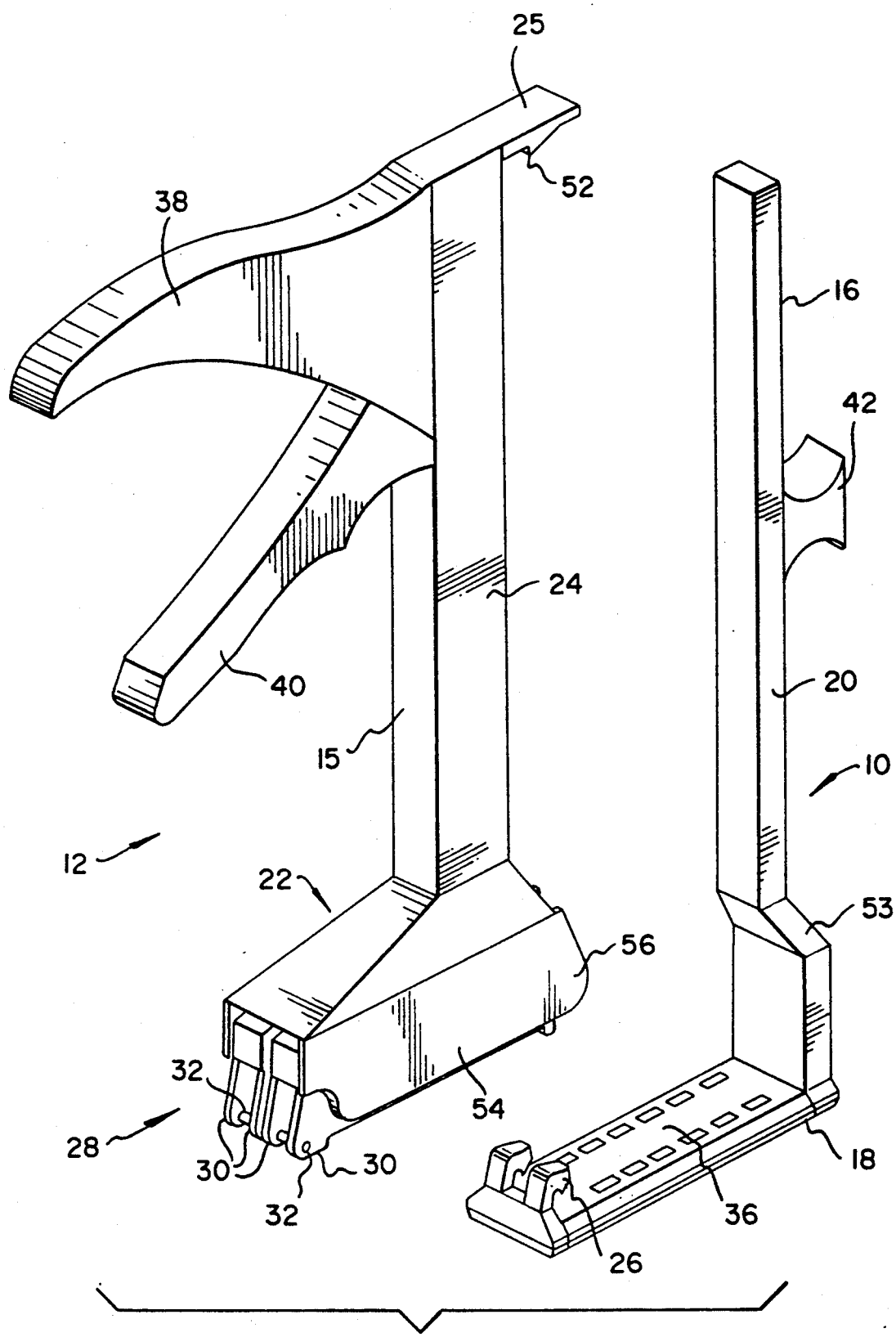
FIG. 1: A side elevational view of a preferred embodiment of the invention.

Referring to the Figures a preferred embodiment of the invention will now be described. The intestinal stapler includes a generally L-shaped base 10 and a generally L-shaped staple actuator arm 12. L-shaped base 10 is formed with a leg 18 and a handle 20 securely fixed at a right angles. Actuator arm 12 is formed with a stapler 22 and an actuator handle 24 which are likewise secured at right angles.

Figure 2:
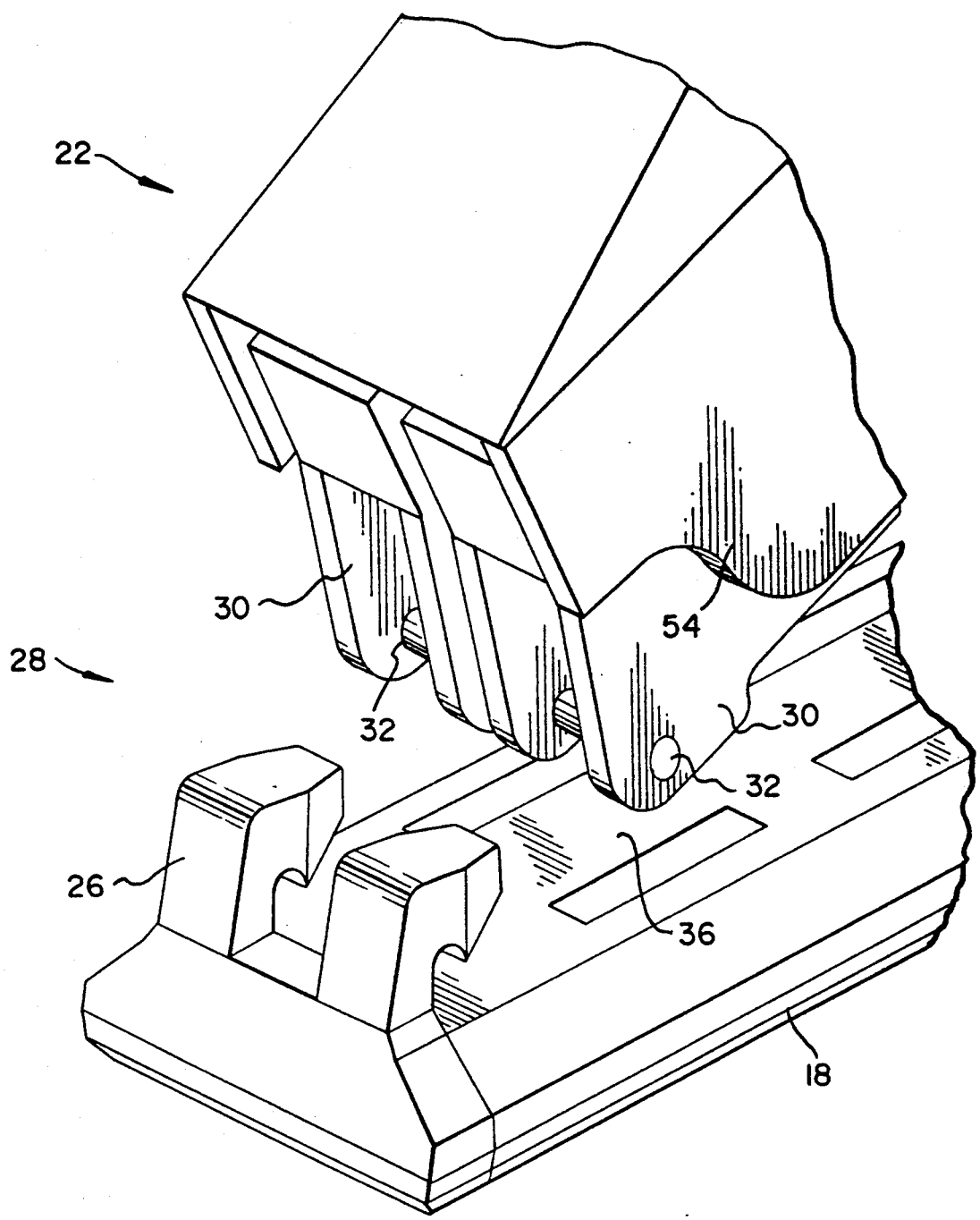
FIG. 2: A perspective view of the attachment means of the embodiment of FIG. 1, showing base and arm members unattached.
Figure 3:
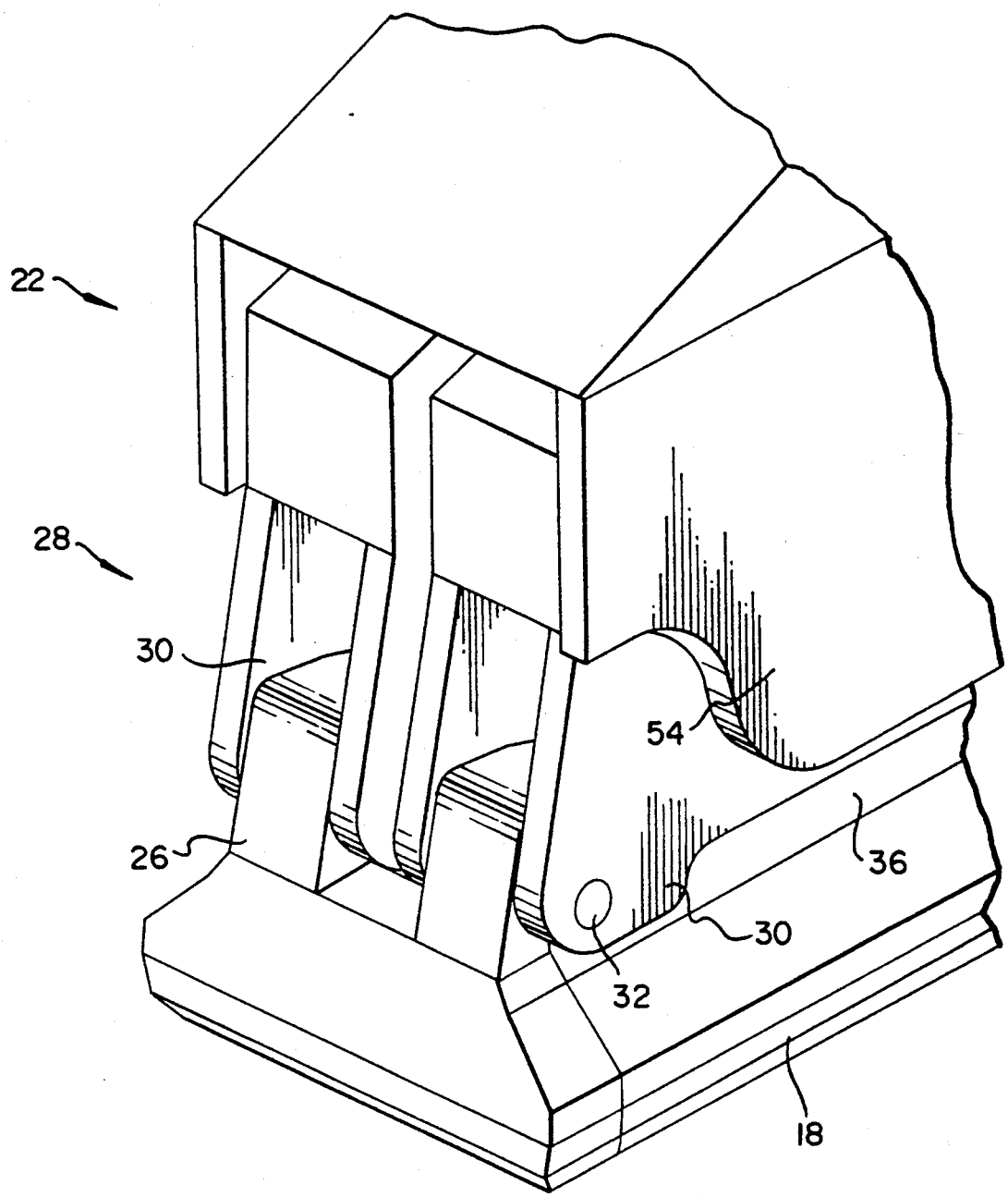
FIG. 3: A perspective view of the attachment means of the embodiment of FIG. 1, showing base and arm members attached.

An attachment means 28 is provided for pivotally, detachably mounting actuator arm 12 to base 10. Attachment means 28, shown most clearly in FIGS. 2 and 3, includes two hook members 26, provided on the end portion of base leg 18 remote from handle 20, and two hook receiving members 27, provided on one end of the bottom surface of actuator carriage 22. Each hook receiving member 27, is formed from two planar brace members 30 secured in spaced relation with a peg 32 secured therebetween. Hook members 26 are, in use, engaged with hook receiving members 27 as seen in FIG. 3 such that actuator arm 12 pivots with respect to base 10 in a plane defined by L-shaped base 10. Planar brace members 30 prevent actuator arm 12 from sliding laterally along pegs 32.

Figure 4:
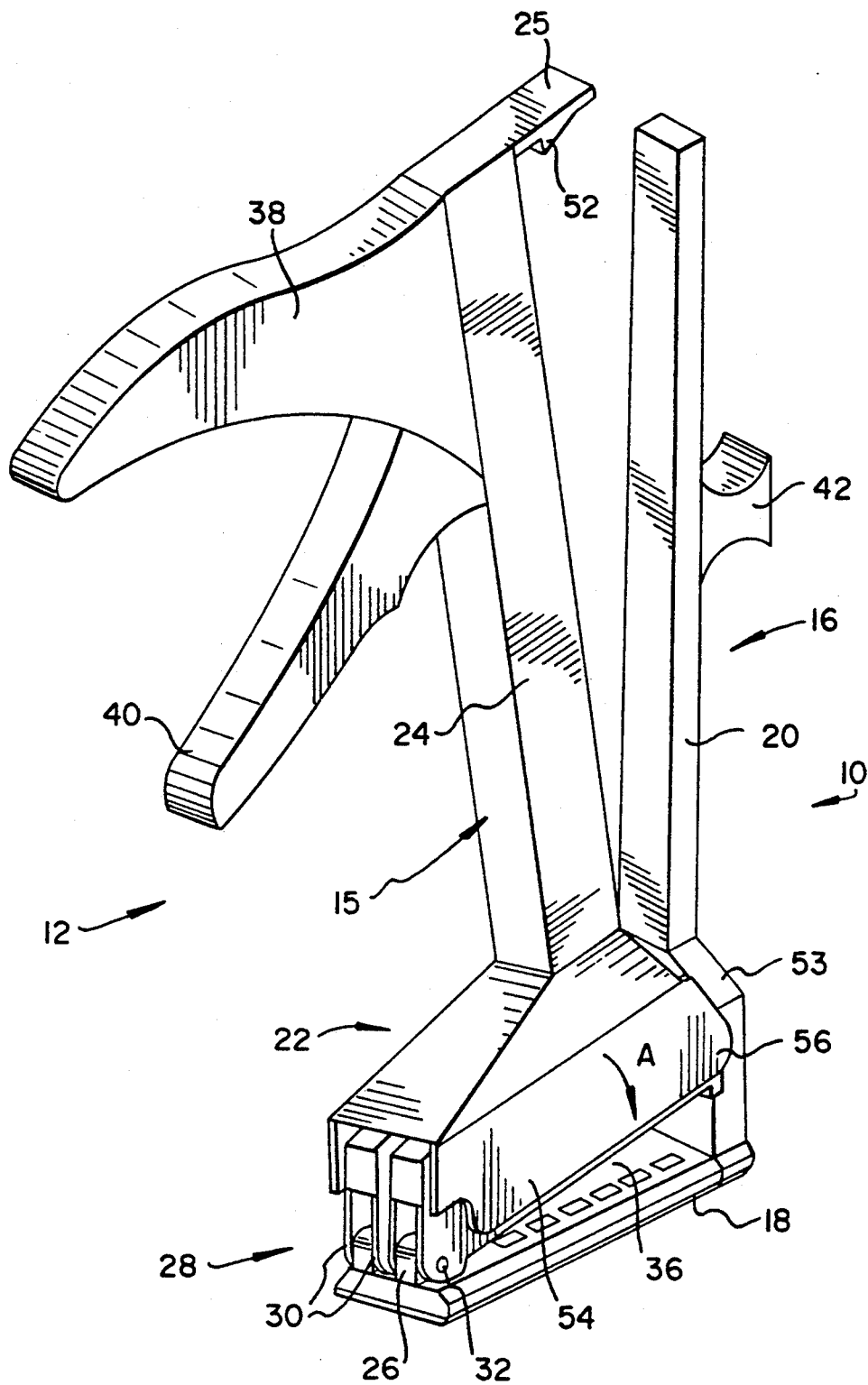
FIG. 4: A perspective view of the embodiment of FIG. 1 showing base and arm members attached in an open position.
Figure 5:
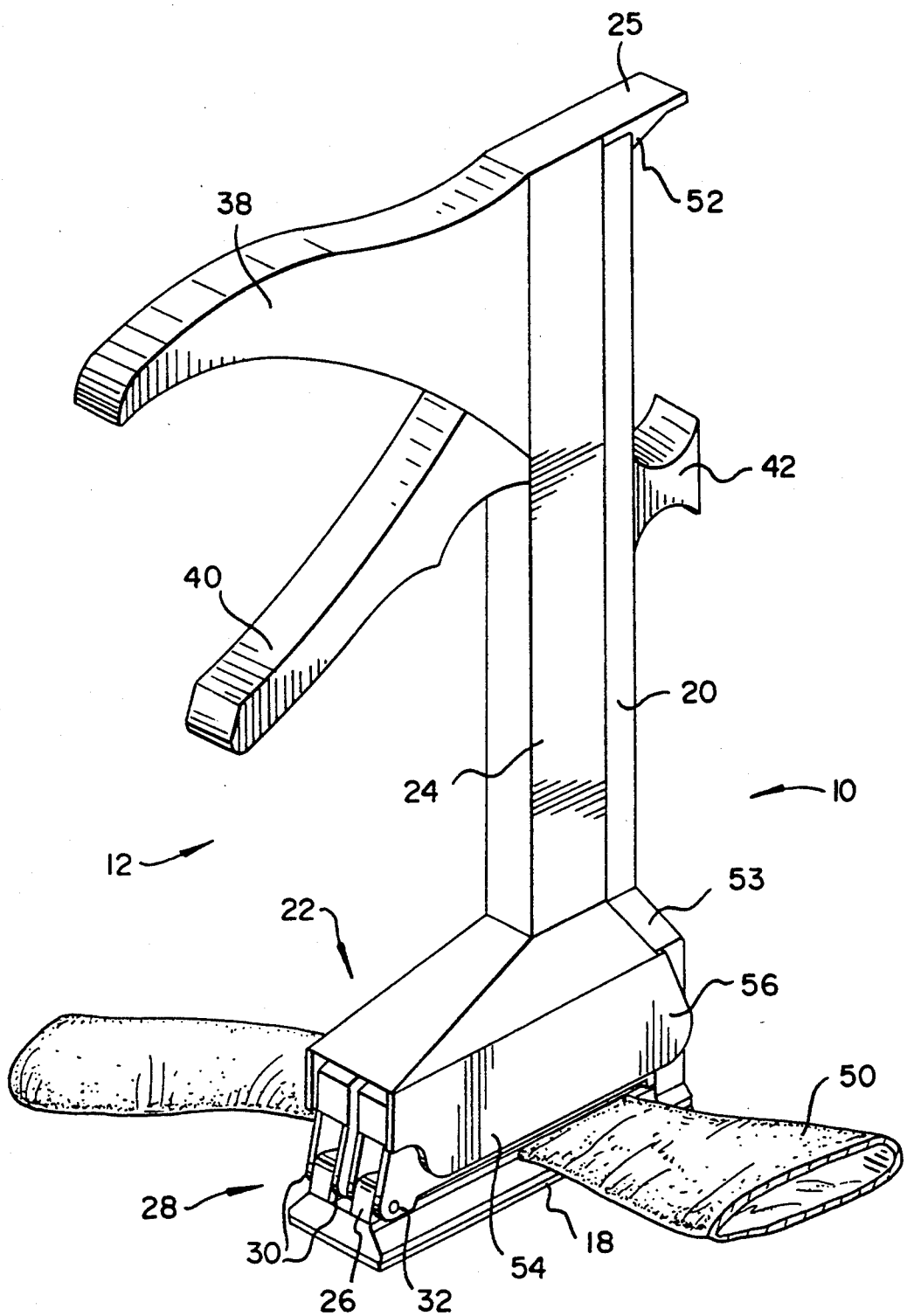
FIG. 5: A perspective view of the embodiment of FIG. 1 showing base and arm members attached in a closed position.

Referring to FIGS. 4 and 5, actuator arm 12 pivots with respect to base 10 along arrow A of FIG. 4 from an open position, wherein a gap is formed between actuator arm 12 and base 10, and a closed position, shown in FIG. 5, wherein actuator arm 12 abuts base 10. In an open position, as shown in FIGS. 1 and 4, the gap between the base 10 and actuator arm 12 is capable of receiving tissue to be stapled such as a bowel or stomach section. When disposed in the closed position of FIG. 5, the gap between the base 10 and actuator 12 is substantially closed with the tissue secured therebetween.

A fastening member 25 extends perpendicular from the top outer edge of actuator handle 24 and includes a detent 52 for receiving and securing the top of base handle 20 as shown in FIG. 5. Fastening member 25 is resilient such that it can be bent upward to release base handle 20.

The inner vertical edge 57 of stapler 22 is angled with respect to actuator handle 24. Base handle 20 includes an angled portion 53 matched to the shape of stapler 22 such that actuator member 24 may be pivoted about pegs 32 when engaged with hooks 26 to fit against the lower end of base handle 20. Also stapler 22 includes side plates 54 having flanges 56 extending beyond the inner-edge of carriage 22 such that, when actuator arm 12 is disposed in the closed position of FIG. 5, flanges 56 abut the side of base handle 20 and thereby prevent lateral movement of actuator arm 12. Thus both fastening members 25 and flanges 56 firmly secure actuator 12 against base 10.

Stapler 22 includes a staple firing mechanism, not shown, for firing staples through the underside of stapler 22.

The staple firing mechanism is of conventional construction and can be similar to, for example, the stapling cartridge disclosed in U.S. Pat. No. 4,354,628 (Green). Preferably, the staple firing mechanism provides for simultaneously firing an array of staples to securely staple the entire cross-section of a bowel section.

An anvil member 36 is formed on the inner edge of base leg 18 such that, when base 10 and actuator 12 are disposed in the closed position of FIG. 5, anvil member 36 is aligned with the staple firing mechanism to receive and clinch staples protruded therefrom.

Preferably, anvil member 36 includes two linear arrays of staple receiving depressions for receiving and clinching a plurality of staples. Both anvil member 36 and the staple firing mechanism are of conventional design.

Actuator handle 24 includes trigger handle 38 and trigger lever 40 for triggering the action of the stapler 22. Trigger handle 38 extends rigidly from the outer edge of handle 24 at an angle below trigger handle 38. Trigger lever 40 extends at an angle from outer edge 15 of actuator handle 24. In use, trigger lever 40 is drawn towards trigger handle 38 to trigger stapler 22. A triggering actuator enclosed within actuator handle 24, connects trigger lever 40 to the staple firing mechanism of stapler 22 and actuates stapler 22. Triggering handle 38, lever 40 and the triggering actuator are also of conventional design and may be similar to, for example, the triggering mechanism disclosed in U.S. Pat. No. 4,354,628 (Green).

To facilitate the handling of the intestinal stapler, a gripping member 42 is provided o the outer edge of base handle 20.

In use, base 10 is inserted into the abdominal cavity of a patient (not shown) such that base leg 18 hooks under a bowel section. Actuator arm 12 is then attached to base leg 18 via attachment means 28, with stapler 22 disposed at an angle with respect to base leg 18. In this open position, actuator arm 12 and base 10 can be moved laterally along the bowel section to precisely position the bowel section. Once the bowel section is properly positioned, actuator arm 12 is pivoted to the closed position of FIG. 5, wherein there is shown an exemplary bowel section 50, and stapler 22 is actuated as described above.

Figure 6:
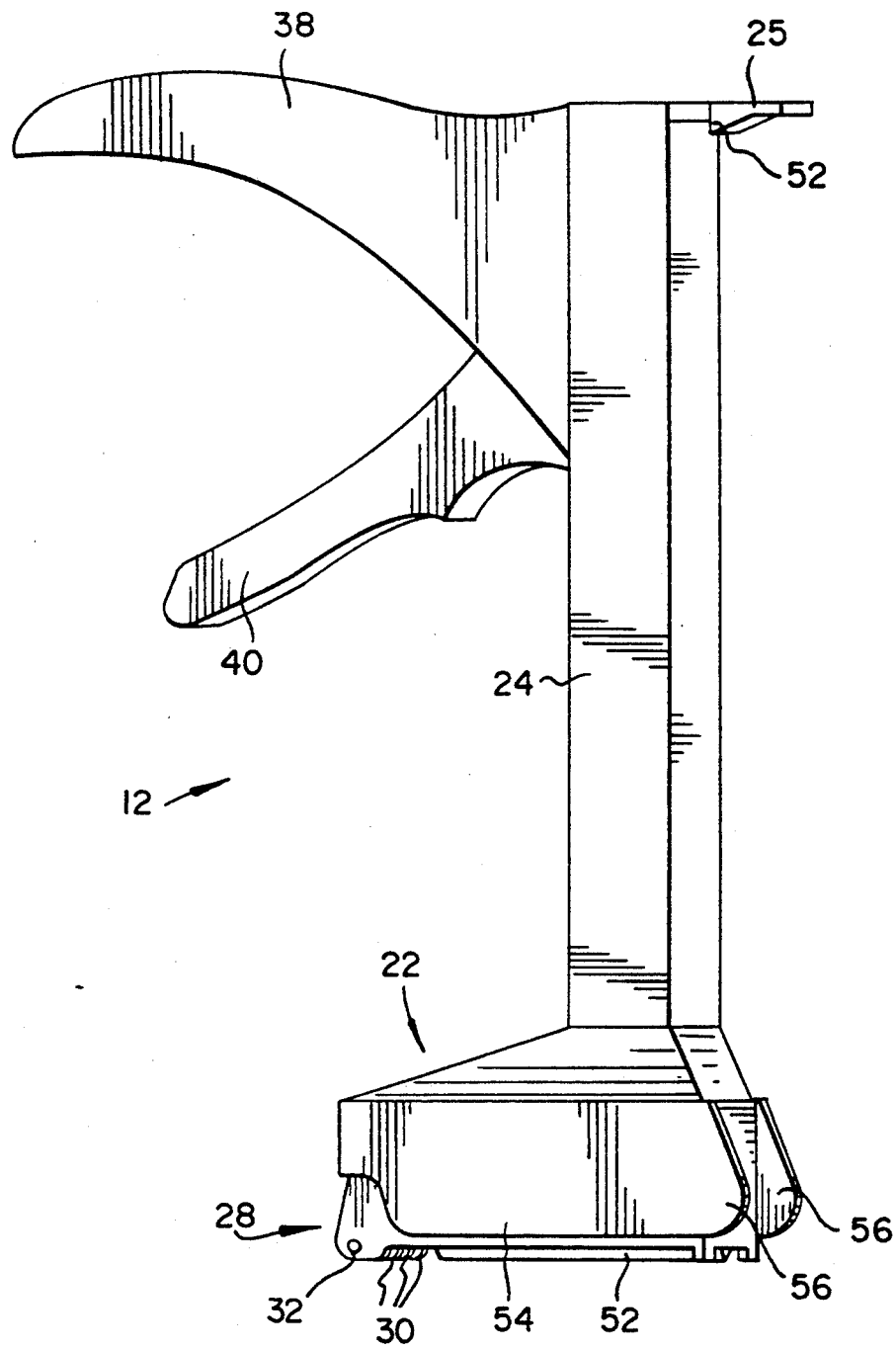
FIG. 6: A side elevational view of an alternative embodiment of the arm member of the embodiment of FIG. 1.

An alternative embodiment of the actuator arm of the invention is shown in FIG. 6, wherein the underside of stapler 22 includes a blade 52 for severing tissue. The embodiment of FIG. 6 is identical to the embodiment of FIGS. 1-5 with the exception of blade 52. For clarity, base 10 is not shown in FIG. 6.

Blade 52 extends laterally along the length of the underside of stapler 22 such that, as actuator arm 12 is pivoted to abut base 10, blade 52 severs enclosed tissue.

Although the invention has been described with respect to exemplary embodiments thereof, it will be understood by those skilled in the art that variations and modifications can be effected in these exemplary embodiments without departing from the scope and spirit of the invention.

What is claimed is:

1. A surgical stapling device comprising a base member and an actuator arm, said base member comprising an anvil and an anvil arm fixed to said anvil and extending at a right angle with respect to said anvil, said actuator arm having a stapler fixed to one end of the actuator arm, a trigger disposed on the opposite end of said actuator arm, attachment means on said stapler and on said anvil for releasably engaging said actuator arm on said anvil for pivotal movement from an open position wherein a gap is provided between the anvil and stapler so as to receive tissue on the anvil and a closed position wherein the tissue is retained on the anvil by the stapler with the anvil arm and actuator arm in face to face engagement.

2. A surgical stapling device according to claim 1 wherein said attachment means comprises a plurality of hook members fixed to one end of said anvil and pins on said stapler for engagement with said hook members.

3. A surgical stapling device according to claim 1 and further including fastening means for securing the actuator arm to the upper end of the anvil arm.

4. A surgical stapling device according to claim 1 and further including blade means mounted on said stapler for severing tissue on said anvil.

5. A surgical stapling device according to claim 1 and further including a pair of rows of staples in said stapler.

* * * * *